(12) United States Patent
Ouchi

(10) Patent No.: US 6,402,687 B1
(45) Date of Patent: Jun. 11, 2002

(54) FULLY-SWALLOWABLE ENDOSCOPIC SYSTEM

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 138 days.

(21) Appl. No.: 09/588,470

(22) Filed: Jun. 6, 2000

(30) Foreign Application Priority Data

Jun. 7, 1999 (JP) .......................................... 11-160030

(51) Int. Cl.$^7$ ................................................. A61B 1/00
(52) U.S. Cl. ...................... 600/139; 600/109; 600/130; 600/141; 600/151
(58) Field of Search .............................. 600/139, 143, 600/151, 152, 101, 109, 128, 130, 136, 141; 348/65, 68, 71, 74

(56) References Cited

U.S. PATENT DOCUMENTS

| | | | | |
|---|---|---|---|---|
| 4,633,304 A | * | 12/1986 | Nagasaki | 128/903 |
| 5,398,670 A | * | 3/1995 | Ortiz et al. | 385/119 |
| 5,595,565 A | * | 1/1997 | Treat et al. | 600/101 |
| 5,604,531 A | * | 2/1997 | Iddan et al. | 348/76 |
| 5,662,587 A | * | 9/1997 | Grundfest et al. | 600/114 |
| 6,162,171 A | * | 12/2000 | Ng et al. | 600/101 |
| 6,240,312 B1 | * | 5/2001 | Alfano et al. | 128/903 |

FOREIGN PATENT DOCUMENTS

| | | | |
|---|---|---|---|
| GB | WO 98/11816 | * | 6/1998 |
| JP | 64-4450 | | 1/1989 |
| JP | 64-76822 | | 3/1989 |
| JP | 3-9705 | | 1/1991 |
| JP | 4-144533 | | 5/1992 |
| JP | 6-114064 | | 4/1994 |
| JP | 7-111985 | | 5/1995 |

\* cited by examiner

Primary Examiner—John P. Leubecker
(74) Attorney, Agent, or Firm—Greenblum & Bernstein, P.L.C.

(57) ABSTRACT

A fully-swallowable endoscopic system includes a rod-shaped endoscope body which can be swallowed entirely by a patient and placed in a body cavity; and a separate external device having no mechanical connection with the rod-shaped endoscope body. The rod-shaped endoscope body includes at least one hard portion each having at least one light emitter and at least one observing system; at least one flexible portion; and at least two bending portions, the at least two bending portions being respectively positioned on the opposite ends of at least one of the at least one flexible portion and being more flexible than the at least one flexible portion. The rod-shaped endoscope body is provided therein with a transmitter for transmitting a radio wave which carries an image formed by the observing system, and a power supplying device. The external device includes a receiver for receiving the radio wave which carries the image.

14 Claims, 7 Drawing Sheets

FULLY-SWALLOWABLE ENDOSCOPIC SYSTEM

BACKGROUND OF THE INVENTION

1. Field of the Invention

The present invention relates to a fully-swallowable endoscopic system which can be retained in the patient's body for a long time, wherein few blind spots occur in an endoscopy examination.

2. Description of the Related Art

In an endoscopy examination, in general, an insertion portion connected to an operation portion is introduced into a patient's body through his or her mouth to observe a target inner part of the body. In the case of observing an inner part of a largely-bent tubular passage in a body such as part of the large intestine, the occurrence of blind spots in the endoscopy examination cannot be avoided.

The body insertion portion of the endoscope must be sometimes inserted and retained in the body for a long time to observe the progress of a diseased part within the body or obtain and/or record somatoscopic information of a patient under ordinary every-day living conditions. However, the insertion and retainment of the endoscope in the body through the patient's mouth causes the patient to suffer from significant pain.

To relieve pain from the patient, it is known to use a capsule type endoscope which is provided at an intermediate portion of a flexible continuous member, as disclosed in Japanese Unexamined Patent Publication No. 64-76822. A patient to be examined swallows a soft ball formed at a tip end of the flexible continuous member the night before the day of examination, so that the soft ball is discharged from the patient's anus the next day. An operator pulls or moves the tip end and the tail end of the flexible continuous member to thereby move or guide the capsule connected to the intermediate portion of the flexible continuous member.

In the capsule type of endoscope described above, the pain that the patient suffers can be eased in comparison with conventional endoscopes. However, the patient must always carry the flexible continuous member whose one end extends out of his or her mouth for more than 12 hours. Consequently, it is impossible for the patient to take a meal or speak. Under these circumstances, no substantial pain relieving effect can be expected. Moreover, it is generally difficult to control the position of the endoscope in the form of a capsule.

SUMMARY OF THE INVENTION

It is an object of the present invention to provide a fully-swallowable endoscopic system which can be easily introduced in a small-radius curved tubular passage in a body, which can relieve a patient to be examined from pain and which makes it possible to observe the target inner part of the body reliably and precisely.

To achieve the object mentioned above, according to the present invention, a fully-swallowable endoscopic system is provided, which includes a rod-shaped endoscope body which can be swallowed entirely by a patient to be examined so as to be placed in a body cavity; and an external device provided separately from the rod-shaped endoscope body having no mechanical connection with the rod-shaped endoscope body. The rod-shaped endoscope body includes in the longitudinal direction thereof at least one hard portion each having at least one light emitter and at least one observing system; at least one flexible portion designed to be bendable along a curve in a body cavity; and at least two bending portions designed to be more flexible than the at least one flexible portion, the at least two bending portions being respectively positioned on the opposite ends of at least one of the at least one flexible portions. The rod-shaped endoscope body is provided therein with a transmitter for transmitting a radio wave which carries an image formed by the observing system, and a power supplying device. The external device includes a receiver for receiving the radio wave which carries the image.

Preferably, one of the at least one hard portion, one of the at least two bending portions, one of the at least one flexible portion, and another one of the at least two bending portions are provided in that order from one end of the rod-shaped endoscope body.

Preferably, one of the at least one hard portion is positioned at one end of the rod-shaped endoscope body, and the at least two bending portions and the at least two flexible portions are alternately arranged, following the one of the at least one hard portion.

Preferably, each of the at least two bending portions can be radio-controlled to bend by an operation of the external device. The rod-shaped endoscope body is provided therein with a radio-controlled driving device which receives a radio operational signal transmitted from the external device to bend the bending portion in accordance with the radio operational signal, and the external device includes an operational portion which is operated to transmit the radio operational signal to the radio-controlled driving device.

Preferably, the radio-controlled driving device includes a plurality of drive wires made of a shape memory alloy, and a selective-heating device which selectively heats the plurality of drive wires to bend the bending portion.

The power supplying device can be a built-in battery.

In an embodiment, the external device includes a microwave transmitter for transmitting a microwave to the rod-shaped endoscope body, wherein the power supplying device converts the microwave into electrical current to supply the electrical current to the rod-shaped endoscope body.

Preferably, the observing system includes an objective optical system and a CCD image sensor.

Preferably, the external device includes a monitor which visually indicates the image.

According to another aspect of the present invention, a fully-swallowable endoscopic system is provided, which includes a rod-shaped endoscope body having a first hard portion, a first bending portion, a first flexible portion, a second bending portion and a second flexible portion, in that order; and a radio controller for manipulating each of the first and second bending portions so as to bend by radio-control. The rod-shaped endoscope body is provided therein with at least one light emitter for illuminating a target inner part of a living body, at least one image pick-up device for taking an image of the target inner part illuminated by the at least one light emitter, and a transmitter for transmitting a radio wave which carries the image taken by the image pick-up device. The first bending portion and the second bending portion are designed to be more flexible than the first flexible portion and the second flexible portion, and one of the at least one light emitter and one of the at least one image pick-up device are positioned in the first hard portion.

In an embodiment, the rod-shaped endoscope body further includes a third bending portion and a second hard portion, wherein the first hard portion, the first bending portion, the first flexible portion, the second bending portion, the second flexible portion, the third bending portion and the second hard portion are arranged in that order from one end to the other end of the rod-shaped endoscope body.

In an embodiment, the another one of the at least one light emitter and another one of the at least one image pick-up device are positioned in the second hard portion.

Preferably, the radio controller includes a monitor and a receiver for receiving the radio wave to indicate the image on the monitor.

In an embodiment, the radio controller further includes a second transmitter for transmitting a microwave to the rod-shaped endoscope body, and wherein the rod-shaped endoscope body is provided therein with a power supplying device which receives the microwave to convert the microwave into electrical current which is to be used as a power source of the rod-shaped endoscope body.

The present disclosure relates to subject matter contained in Japanese Patent Application No.11-160030 (filed on Jun. 7, 1999) which is expressly incorporated herein by reference in its entirety.

BRIEF DESCRIPTION OF THE DRAWINGS

The invention will be discussed below in detail with reference to the drawings, in which.

DESCRIPTION OF THE PREFERRED EMBODIMENTS

Figure 1:
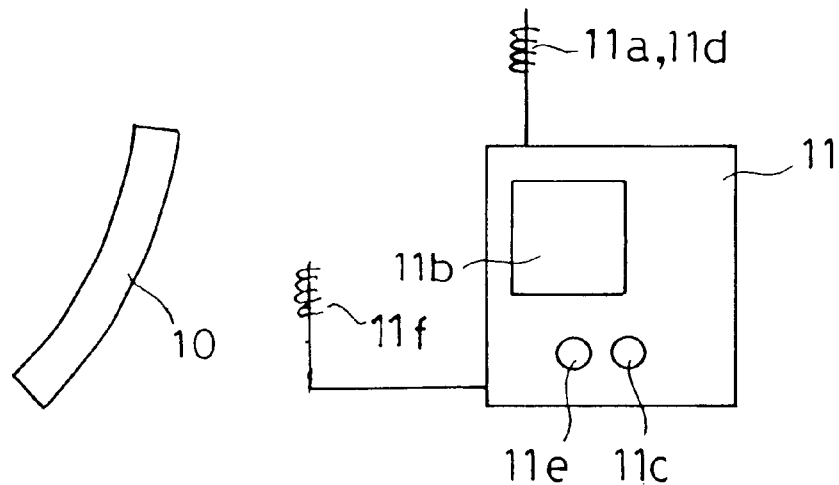
FIG. 1 is a schematic view of an embodiment of an fully-swallowable endoscopic system comprising a rod-shaped endoscope body and an external device, according to the present invention.

FIG. 1 shows an embodiment of a fully-swallowable endoscopic system which includes a rod-shaped endoscope body 10 and an external device 11. A patient to be examined swallows the rod-shaped endoscope body 10 before an endoscopic examination is performed with the endoscope 10. The external device 11 functions as a wireless controller (radio controller) and a power supply for the endoscope 10.

Figure 3:
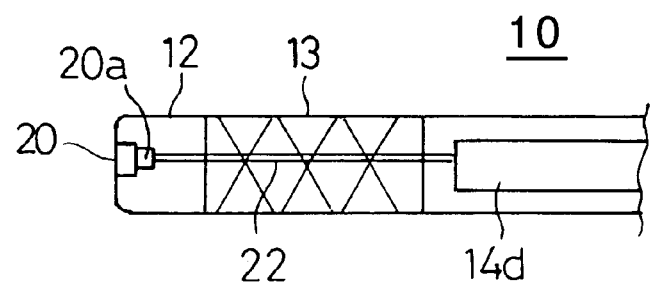
FIG. 3 is a schematic cross sectional view of part of the rod-shaped endoscope body shown in FIG. 2, taken along a different plane.
Figure 2:
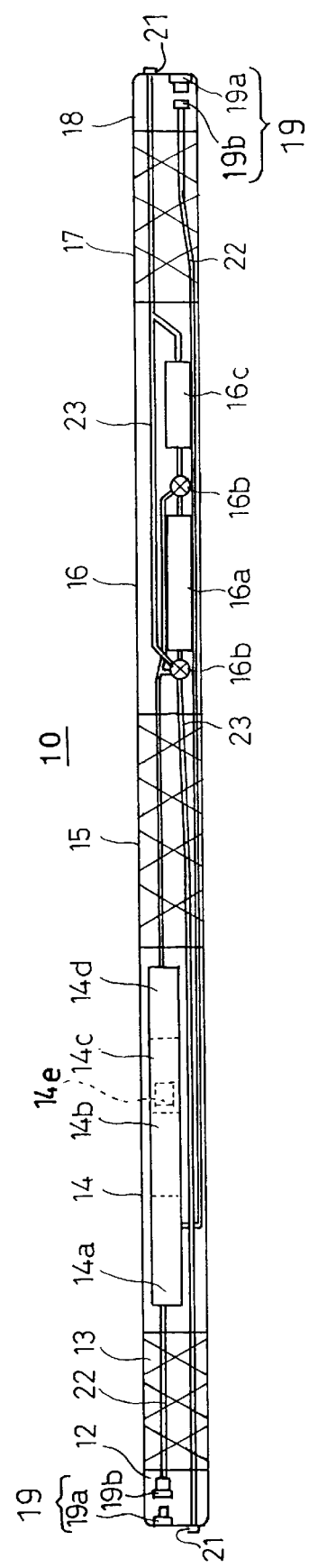
FIG. 2 is a schematic cross sectional view of the first embodiment of the rod-shaped endoscope body, according to the present invention.
Figure 4:
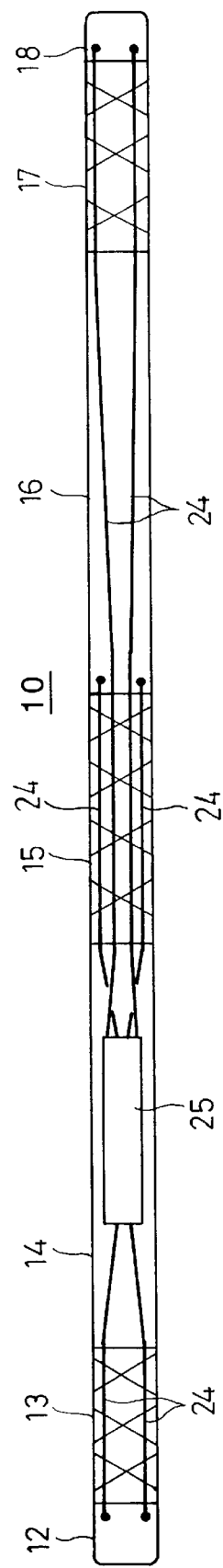
FIG. 4 is a schematic cross sectional view of the rod-shaped endoscope body shown in FIG. 2, showing a radio-controlled driving device thereof.

FIGS. 2 through 4 show the first embodiment of the rod-shaped endoscope body 10. The rod-shaped endoscope body 10 is provided with a first hard portion (unbendable portion) 12, a first bending portion 13, a first flexible portion 14, a second bending portion 15, a second flexible portion 16, a third bending portion 17 and a second hard portion (unbendable portion) 18, in this order from the front end (the left end as viewed in FIG. 2). The rod-shaped endoscope body 10 is entirely covered by an elastic covering 28 whose outer surface is smooth and well-slidable (see FIG. 10). The first and second hard portions 12 and 18 are each made of a hard material (e.g., a hard plastic) which is not macroscopically deformable. Each of the first and second flexible portions 14 and 16 is designed to be bendable along the shape of a digestive tract when it is inserted in the body cavity.

Each of the hard portions 12 and 18 is provided therein with an observing system 19, an illumination window 20 and an air/water supply port 21. Each observing system 19 includes an objective optical system 19a and a CCD image sensor 19b. The first flexible portion 14 is provided therein with an amplifier circuit 14a, a transmitter/receiver device 14b, a power supplying device 14c, a control circuit 14d and a microwave receiver 14e. Each CCD image sensor 19b is connected to the amplifier circuit 14a via a corresponding signal line 22. The amplifier circuit 14a is connected to the transmitter/receiver device 14b, which is positioned in the first flexible portion 14. Each of the hard portions 12 and 18 is provided therein with an LED (light emitter) 20a secured to the corresponding illumination window 20. Each LED 20a is connected to the control circuit 14d via a corresponding signal line 22 (see FIG. 3).

The second flexible portion 16 is provided therein with a compressed air tank 16a and a water tank 16c which are each provided with a corresponding valve 16b. Each air/water supply port 21 is connected to the outer end of a corresponding air/water supply tube 23. The inner end of each air/water supply tube 23 is connected to the corresponding valve 16b. Each valve 16b is controlled to open or shut by the control circuit 14d. The power supplying device 14c is connected to the transmitter/receiver device 14b and the control circuit 14d. The power supplying device 14c converts a microwave received by the microwave receiver 14e into electrical current to supply the same to the transmitter/receiver device 14b and the control circuit 14d. The microwave received by the microwave receiver 14e is transmitted from the external device 11.

Figure 10:
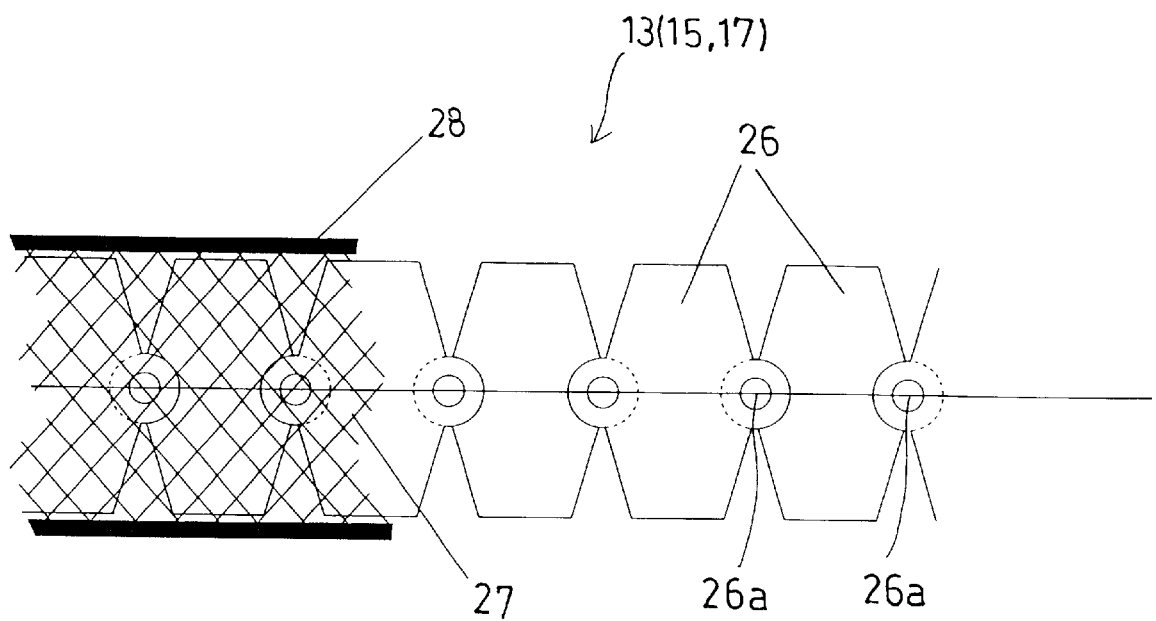
FIG. 10 is a schematic side view of part of the first embodiment of the bending portion, with parts omitted for clarity, in the case where the bending portion is designed to be bendable in a single plane.

FIG. 10 shows part of the first embodiment of each of the first, second and third bending portions 13, 15 and 17 in the case where each bending portion is designed to be bendable in a single plane. The first embodiment of each bending portion is provided with an articulated series of ring joints 26. Adjacent ring joints 26 are connected with each other by a shaft 26a so that each of the adjacent ring joints 26 can rotate about the shaft 26a. All the shafts 26a are parallel to one another so as to lie in a common plane. The articulated series of ring joints 26 having such a structure is covered by a steel wired tube 27. This steel wired tube 27 is covered by the aforementioned elastic covering 28. Each of the first, second and third bending portions 13, 15 and 17 is designed to be more flexible and bendable than the first and second flexible portions 14 and 16.

The rod-shaped endoscope body 10 is provided therein with a plurality of bendable drive wires (two wires in the first embodiment of the first bending portion 13) 24 which extend within the first bending portion 13 and the first flexible portion 14 (see FIG. 4). Each drive wire 24 is made of a shape memory alloy (SMA) which bends when supplied with electrical current to be heated. The rod-shaped endoscope body 10 is further provided therein with a selective-heating device 25 which is connected to the transmitter/receiver device 14b. The drive wires 24, the selective heating device 25, and the transmitting/receiving device 14b constitute a radio-controlled driving device. The tips (outer ends) of the drive wires 24 are each secured to the first hard portion 12, while the inner ends of the same are each secured to the selective-heating device 25.

The two drive wires 24 are diametrically arranged at opposite sides of the axis of the cylindrical first bending portion 13. The selective-heating device 25 is a circuit which selectively supplies electrical current to the two drive wires 24 to heat the same in accordance with control signals output from the transmitter/receiver device 14b, which makes it possible to bend the first bending portion 13 in a plane in which the two drive wires 24 lie.

Figure 9:
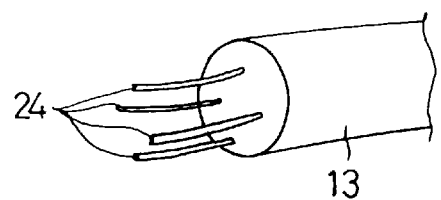
FIG. 9 is an explanatory view of part of the second embodiment of the bending portion of the rod-shaped endoscope body, showing an arrangement of the bendable drive wires provided in the bending portion.
Figure 11:
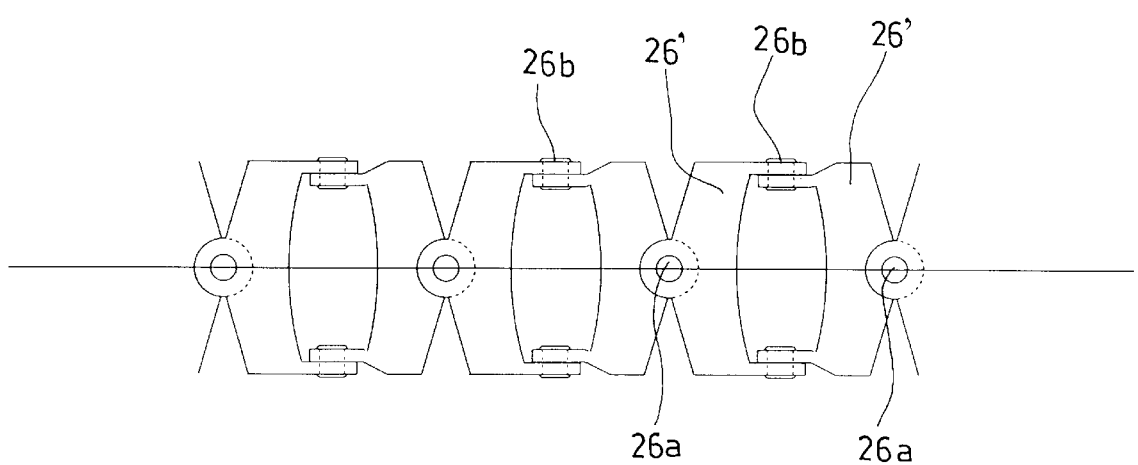
FIG. 11 is a schematic side view of part of the second embodiment of the bending portion, in the case where the bending portion is designed to be bendable in two planes perpendicular to each other.

When it is required that the first bending portion 13 be bendable only in a single plane, it is sufficient that the rod-shaped endoscope body 10 be provided with the first embodiment of the first bending portion 13, as shown in FIG. 10, which can bend only in a single plane. When it is required that the first bending portion 13 be bendable in two planes perpendicular to each other, the first bending portion 13 needs to have a structure such as shown in FIG. 11. FIG. 11 shows part of the second embodiment of each of the first, second and third bending portions 13, 15 and 17 in the case where it is designed to be bendable in two planes perpendicular to each other. The second embodiment of each bending portion is provided with an articulated series of ring joints 26'. Adjacent ring joints 26' are connected with each other by a first shaft 26a or a second shaft 26b so that each of the adjacent ring joints 26' can rotate about each of the shafts 26a and 26b. The first and second shafts 26a and 26b extend in directions perpendicular to each other and are alternately arranged. In FIG. 11, neither the steel wired tube 27 nor the aforementioned elastic covering 28 is illustrated for clarity of illustration. In the second embodiment of the first bending portion 13, four bendable drive wires 24 extend within the first bending portion 13 and the first flexible portion 14 (see FIG. 9). The tips (outer ends) of the four drive wires 24 are each secured to the first hard portion 12 at 90° intervals about the axis of the first hard portion 12. The inner ends of each pair of drive wires 24 which radially face each other are secured to the selective-heating device 25. In the second embodiment of the first bending portion 13, although only two drive wires 24 are shown in FIG. 4, the remaining two drive wires 24 are provided in a similar manner.

Each of the second and third bending portions 15 and 17 is controlled to bend similar to the first bending portion 13. Namely, the rod-shaped endoscope body 10 is provided therein with another plurality of bendable drive wires (two wires when the bending portion needs to be bendable only in a single plane, or four drive wires when the bending portion needs to be bendable in two planes perpendicular to each other) 24 for each of the second and third bending portions 15 and 17 (see FIG. 4). The structure of the mechanism for driving the first bending portion 13 using the drive wires 24 is substantially identical to the mechanism for driving each of the second and third bending portions 15 and 17 except that the tips of the drive wires 24 for manipulating the second bending portion 15 are each secured to the second flexible portion 16 while the tips of the drive wires 24 for manipulating the third bending portion 17 are each secured to the second hard portion 18, whereas the tips of the drive wires 24 for manipulating the first bending portion 13 are each secured to the first hard portion 12.

The external device 11 shown in FIG. 1 is provided with an external receiving portion 11a, a monitor 11b, a bending portion controller portion (operational portion) 11c, an external transmitting portion 11d, a valve controlling portion 11e and a microwave transmitting portion (microwave transmitter) 11f. The external device 11 transmits the aforementioned microwave, which is used as a power supply for the rod-shaped endoscope body 10, from the microwave transmitting portion 11f to the rod-shaped endoscope body 10. This transmitted microwave is received by the microwave receiver 14e and is converted into electrical current by the power supplying device 14c. The power supplying device 14c supplies the electrical current to the transmitter/receiver device 14b and the control circuit 14d. By manually operating the bending portion controller portion 11c and the valve controlling portion 11e of the external device 11, radio operational signals for operating the first, second or second bending portion 13, 15 or 17 and the valve 16b are generated by the external device 11 to be transmitted to the rod-shaped endoscope body 10 via the external transmitting portion 11d. The external receiving portion 11a receives image signals (radio waves) transmitted from the transmitter/receiver device 14b. The received image signals are displayed on the monitor 11b to be observed by an operator.

Figure 5:
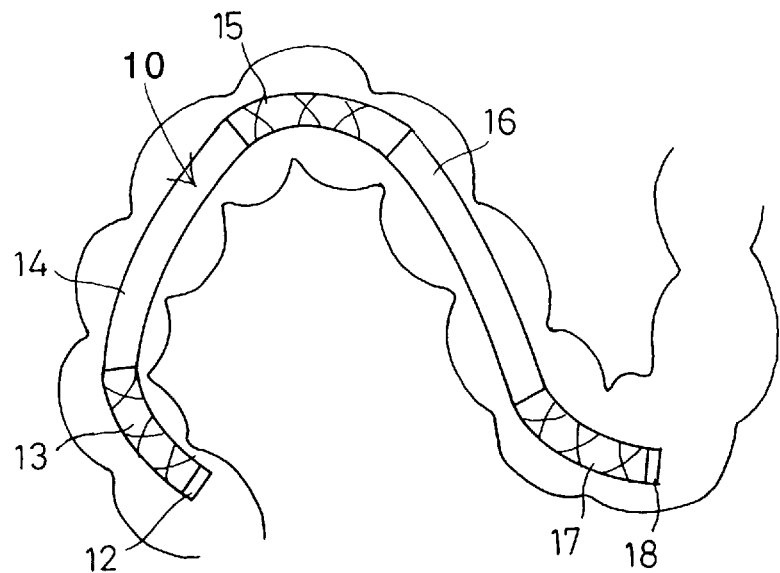
FIG. 5 is an explanatory view of the rod-shaped endoscope body shown in FIG. 2, showing a state where the endoscope is introduced into the large intestine.

In the endoscope constructed as above, a patient to be examined swallows the rod-shaped endoscope body 10 entirely from the front end thereof, i.e., from the first hard portion 12. After being swallowed entirely, the rod-shaped endoscope body 10 is radio-controlled to proceed gradually along the alimentary canal by peristalsis. Even if the endoscope 10 is in a winding alimentary canal as shown in FIG. 5, the endoscope 10 can easily move since it is provided at intermediate part thereof with the second bending portion 15. Once the rod-shaped endoscope body 10 reaches a target inner part of the body, it can be observed via the rod-shaped endoscope body 10 and at the same time the necessary information about a living body can be collected in a manner such as the following.

In the present embodiment of the fully-swallowable endoscopic system, the transmitter/receiver device 14b of the rod-shaped endoscope body 10 receives the radio operational signals transmitted from the external transmitting portion lid of the external device 11 so that each of fundamental operational elements of the rod-shaped endoscope body 10 can be radio-controlled by operating the external device 11. The power supplying device 14c supplies electrical current to the transmitter/receiver device 14b and the control circuit 14d by converting the received microwave into the electrical current, so that the operator does not have to care about the remaining battery power of the rod-shaped endoscope body 10. This makes it possible to observe the target inner part of the body sufficiently.

Each LED 20*a*, which receives power from the power supplying device 14*c* via the corresponding signal line 22, emits light outwardly through the corresponding illumination window 20. The object image upon which the illumination light of each LED 20*a* is impinged is formed on the sensitive surface of the corresponding CCD image sensor 19*b* through the corresponding objective optical system 19*a*. The image signal supplied from each CCD image sensor 19*b* is amplified by the amplifier circuit 14*a*. This amplified image signal is transmitted from the transmitter/receiver device 14*b* to be subsequently received by the external receiving portion 11*a* of the external device 11. The image signal received by the external device 11 is observed on the monitor 11*b*. The operator operates the bending portion controller portion 11*c* of the external device 11 to bend the first bending portion 13 or the third bending portion 17 via the selective-heating device 25, which is controlled by the radio operational signals transmitted from the external transmitting portion 11*d*, to thereby change the direction of the objective optical system 19*a* to observe the target inner part of the body. At this time, the compressed air in the compressed air tank 16*a* or the water charged in the water tank 16*c* can be sent to the air/water supply port 21 via the corresponding air/water supply tube 23 by operating the valve controlling portion 11*e* of the external device 11, so that the transmitter/receiver device 14*b* receives the radio operational signals transmitted from the external transmitting portion 11*d*, so as to operate the corresponding valve 16*b*.

Figure 6:
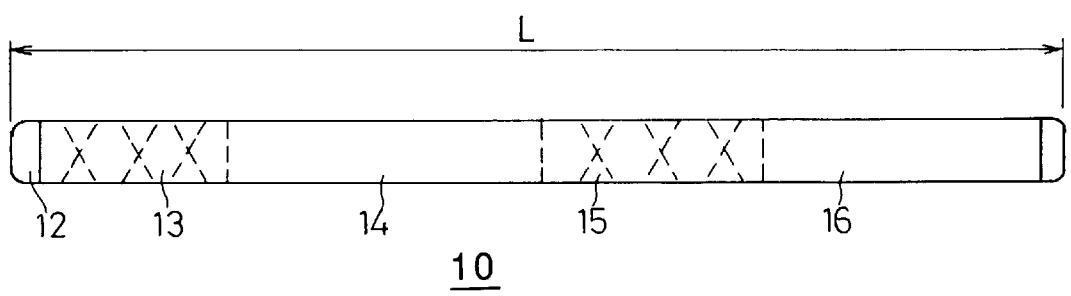
FIG. 6 is a schematic side view of the second embodiment of the rod-shaped endoscope body, according to the present invention.
Figure 7:
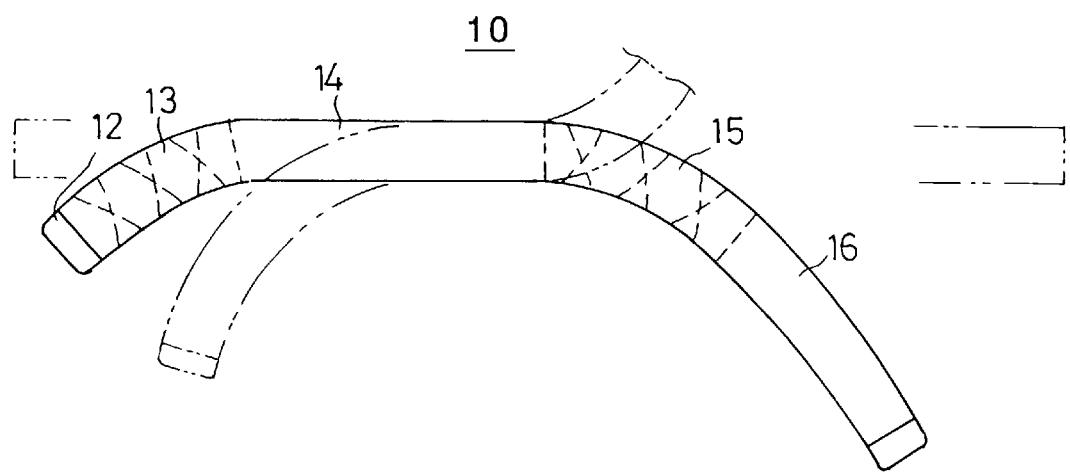
FIG. 7 is a schematic side view of the rod-shaped endoscope body shown in FIG. 6, showing a state where both the front and rear bending portions are bent.
Figure 8:
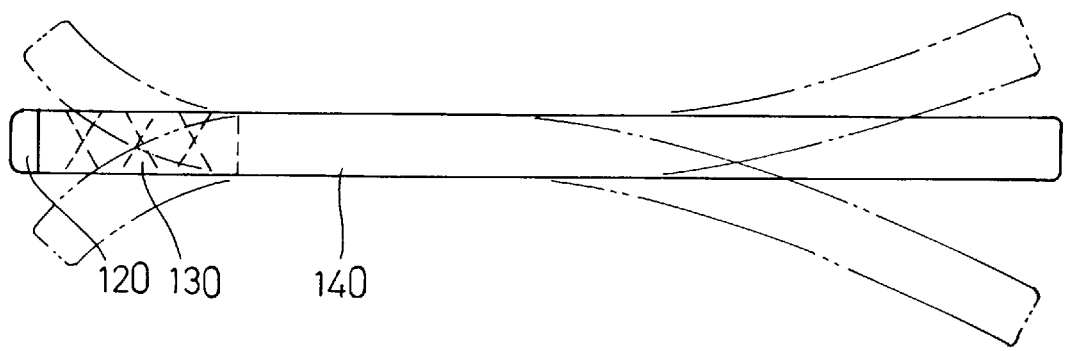
FIG. 8 is a schematic side view of a comparative example of a rod-shaped endoscope body which is to be compared with the rod-shaped endoscope body shown in FIGS. 6 and 7, showing that the rod-shaped endoscope body shown in FIGS. 6 and 7 according to the present invention has more bending capability.

The rod-shaped endoscope body 10 can bend largely so as to have a small-radius curve, as can be seen from FIGS. 6 through 8. FIG. 6 shows the second embodiment of the rod-shaped endoscope body 10, according to the present invention, which is provided with a first hard portion 12, a first bending portion 13, a first flexible portion 14, a second bending portion 15, a second flexible portion 16 in this order from the front end (the left end as viewed in FIG. 6). FIG. 7 shows the second embodiment of the rod-shaped endoscope body 10 in a state where each of the front and rear bending portions thereof bends. This second embodiment of the endoscope 10 is substantially identical to the first embodiment of the endoscope 10 shown in FIG. 2 except that second embodiment of the endoscope 10 is not provided with a third bending portion or a second hard portion which correspond to the third bending portion 17 or the second hard portion 18, respectively. FIG. 8 shows a comparative example of a rod-shaped endoscope body. This endoscope is provided with a hard portion 120, a bending portion 130 and a flexible portion 140 which correspond to the hard portion 12, the bending portion 13 and the flexible portion 14 of the first embodiment of the rod-shaped endoscope body 10, respectively, in this order from the front end (the left end as viewed in FIG. 8). The length of the endoscope shown in FIG. 8 is the same as that of the first embodiment of the endoscope 10. It can be appreciated by comparing the endoscope shown in FIG. 7 with the endoscope shown in FIG. 8 that the rod-shaped endoscope body 10 can bend largely so as to have a small-radius curve because the endoscope 10 is provided at intermediate part thereof with the second bending portion 15.

The power supplying device 14*c* of the rod-shaped endoscope body 10 can be replaced by a built-in battery to simplify the structure of endoscopic system.

As can be understood from the foregoing, according to the rod-shaped endoscope body to which the present invention is applied, since the rod-shaped endoscope body is entirely positioned in a body cavity without any cables or wires which connect the rod-shaped endoscope body with the external device, a patient to be examined does not suffer from pain even if the endoscope is retained in the patient's body for a long time. Furthermore, since the endoscope 10 is provided at intermediate part thereof with a bending portion, the endoscope can be easily introduced and move in a small-radius curved tubular passage in a body, wherein few blind spots occur in an endoscopy examination.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A fully-swallowable endoscopic system comprising:

a rod-shaped endoscope body which can be swallowed entirely by a patient to be examined so as to be placed in a body cavity; and an external device provided separately from said rod-shaped endoscope body having no mechanical connection with said rod-shaped endoscope body;

wherein said rod-shaped endoscope body includes in the longitudinal direction thereof at least one hard portion each having at least one light emitter and at least one observing system; at least one flexible portion designed to be bendable along a curve in a body cavity; and at least two bending portions designed to be more flexible than said at least one flexible portion, said at least two bending portions being respectively positioned on the opposite ends of at least one of said at least one flexible portion;

wherein said rod-shaped endoscope body is provided therein with a transmitter for transmitting a radio wave which carries an image formed by said observing system, and a power supplying device; and wherein said external device comprises a receiver for receiving said radio wave which carries said image.

2. The fully-swallowable endoscopic system according to claim 1, wherein one of said at least one hard portion, one of said at least two bending portions, one of said at least one flexible portion, and another one of said at least two bending portions are provided in that order from one end of said rod-shaped endoscope body.

3. The fully-swallowable endoscopic system according to claim 1, wherein one of said at least one hard portion is positioned at one end of said rod-shaped endoscope body, and wherein said at least two bending portions and said at least one flexible portion are alternately arranged, following said one of said at least one hard portion.

4. The fully-swallowable endoscopic system according to claim 1, wherein each of said at least two bending portions can be radio-controlled to bend by an operation of said external device;

wherein said rod-shaped endoscope body is provided therein with a radio-controlled driving device which receives a radio operational signal transmitted from said external device to bend said bending portion in accordance with said radio operational signal, and wherein said external device comprises an operational portion which is operated to transmit said radio operational signal to said radio-controlled driving device.

5. The fully-swallowable endoscopic system according to claim 4, wherein said radio-controlled driving device comprises a plurality of drive wires made of a shape memory alloy, and a selective-heating device which selectively heats said plurality of drive wires to bend said bending portion.

6. The fully-swallowable endoscopic system according to claim 1, wherein said power supplying device comprises a built-in battery.

7. The fully-swallowable endoscopic system according to claim 1, wherein said external device comprises a microwave transmitter for transmitting a microwave to said rod-shaped endoscope body, and wherein said power supplying device converts said microwave into electrical current to supply said electrical current to said rod-shaped endoscope body.

8. The fully-swallowable endoscopic system according to claim 1, wherein said observing system comprises an objective optical system and a CCD image sensor.

9. The fully-swallowable endoscopic system according to claim 1, wherein said external device comprises a monitor which visually indicates said image.

10. A fully-swallowable endoscopic system comprising:

a rod-shaped endoscope body which comprises a first hard portion, a first bending portion, a first flexible portion, a second bending portion and a second flexible portion, in that order; and a radio controller for manipulating each of said first and second bending portions so as to bend by radio-control;

wherein said rod-shaped endoscope body is provided therein with at least one light emitter for illuminating a target inner part of a living body; at least one image pick-up device for taking an image of said target inner part illuminated by said at least one light emitter; and a transmitter for transmitting a radio wave which carries said image taken by said image pick-up device;

wherein said first bending portion and said second bending portion are designed to be more flexible than said first flexible portion and said second flexible portion, and wherein one of said at least one light emitter and one of said at least one image pick-up device are positioned in said first hard portion.

11. The fully-swallowable endoscopic system according to claim 10, wherein said rod-shaped endoscope body further comprises a third bending portion and a second hard portion, wherein said first hard portion, said first bending portion, said first flexible portion, said second bending portion, said second flexible portion, said third bending portion and said second hard portion are arranged in that order from one end to the other end of said rod-shaped endoscope body.

12. The fully-swallowable endoscopic system according to claim 11, wherein said another one of said at least one light emitter and another one of said at least one image pick-up device are positioned in said second hard portion.

13. The fully-swallowable endoscopic system according to claim 10, wherein said radio controller comprises a monitor and a receiver for receiving said radio wave to indicate said image on said monitor.

14. The fully-swallowable endoscopic system according to claim 10, wherein said radio controller further comprises a second transmitter for transmitting a microwave to said rod-shaped endoscope body, and wherein said rod-shaped endoscope body is provided therein with a power supplying device which receives said microwave to convert said microwave into electrical current which is to be used as a power source of said rod-shaped endoscope body.

* * * * *